United States Patent
Leiner et al.

(10) Patent No.: US 8,040,496 B2
(45) Date of Patent: Oct. 18, 2011

(54) SYSTEM AND METHOD FOR AN ILLUMINATION-QUALITY TEST

(75) Inventors: Dennis C. Leiner, Cape Elizabeth, ME (US); Michael Bush, South Portland, ME (US); David J. Biolsi, Portland, ME (US)

(73) Assignee: Lighthouse Imaging Corporation, Portland, ME (US)

( * ) Notice: Subject to any disclaimer, the term of this patent is extended or adjusted under 35 U.S.C. 154(b) by 382 days.

(21) Appl. No.: 11/687,192

(22) Filed: Mar. 16, 2007

(65) Prior Publication Data
US 2008/0228031 A1    Sep. 18, 2008

(51) Int. Cl.
*G01N 21/00*   (2006.01)
*G01B 9/00*    (2006.01)
*G01J 1/40*    (2006.01)
*G01J 1/00*    (2006.01)

(52) U.S. Cl. .... 356/73.1; 356/124; 356/236; 356/239.1; 250/228

(58) Field of Classification Search .......................... None
See application file for complete search history.

(56) References Cited

U.S. PATENT DOCUMENTS

| | | | | |
|---|---|---|---|---|
| 2,419,421 A * | 4/1947 | Sachtleben | | 356/124 |
| 3,436,556 A * | 4/1969 | McCartney | | 250/223 R |
| 4,326,869 A * | 4/1982 | Kurosaki et al. | | 65/412 |
| 4,544,242 A * | 10/1985 | Schindl | | 359/211.1 |
| 4,722,337 A * | 2/1988 | Losch et al. | | 606/16 |
| 4,915,500 A * | 4/1990 | Selkowitz | | 356/221 |
| 4,932,779 A * | 6/1990 | Keane | | 356/319 |
| 4,939,376 A * | 7/1990 | Woodruff et al. | | 250/554 |
| 5,098,195 A * | 3/1992 | Halyo et al. | | 374/9 |
| 5,190,536 A * | 3/1993 | Wood et al. | | 606/16 |
| 5,237,403 A * | 8/1993 | Sugimoto et al. | | 348/69 |
| 5,251,004 A * | 10/1993 | Doiron et al. | | 356/236 |
| 5,359,406 A * | 10/1994 | Suzuki | | 356/236 |
| 5,820,547 A | 10/1998 | Strobl et al. | | |
| 5,971,576 A * | 10/1999 | Tomioka et al. | | 362/574 |
| 6,191,891 B1 | 2/2001 | Pellicori | | |
| 6,203,492 B1* | 3/2001 | Davis | | 600/101 |
| 6,260,994 B1* | 7/2001 | Matsumoto et al. | | 362/574 |
| 6,369,883 B1* | 4/2002 | Clark | | 356/73.1 |
| 6,498,642 B1* | 12/2002 | Duckett | | 356/244 |
| 6,564,089 B2* | 5/2003 | Izatt et al. | | 600/478 |
| 6,673,011 B1* | 1/2004 | Hilger | | 600/117 |
| 6,734,958 B1 | 5/2004 | Mackinnon et al. | | |
| 6,833,912 B2* | 12/2004 | Lei et al. | | 356/124 |
| 6,862,085 B2* | 3/2005 | Hirt et al. | | 356/73.1 |
| 7,022,065 B2* | 4/2006 | Leiner et al. | | 600/101 |
| 7,477,458 B2* | 1/2009 | Nakamura | | 359/707 |
| 2003/0133101 A1* | 7/2003 | Kubo | | 356/236 |

FOREIGN PATENT DOCUMENTS

JP          08094943 A   *   4/1996

* cited by examiner

*Primary Examiner* — Tarifur Chowdhury
*Assistant Examiner* — Gordon Stock, Jr.
(74) *Attorney, Agent, or Firm* — Pierce Atwood LLP

(57) ABSTRACT

An endoscopic illumination tester is provided for testing illumination quality of a light source. The endoscopic illumination tester includes an optical bridge that is removably interlockable with the light source. The endoscopic illumination tester includes an integrating sphere that is removably interlockable with the optical bridge. The endoscopic illumination tester may further engage a light guide connectable between the optical bridge and the light source. An endoscope may be inserted between the optical bridge and the integrating sphere.

20 Claims, 6 Drawing Sheets

SYSTEM AND METHOD FOR AN ILLUMINATION-QUALITY TEST

FIELD OF THE INVENTION

The present invention is generally related to testing of optics devices and, more particularly, is related to a device for testing illumination quality of an optics device.

BACKGROUND OF THE INVENTION

The United States endoscopy market size in 1999 was $3.6 Billion.

Visualization products, which include rigid endoscopes, light sources and video accessories, represented approximately 17% of this market, in some estimations, valued at more than $600 Million. According to Stryker Corporation's 1999 Fact Book, the world endoscopy market approaches $6 Billion, and the market for visualization products continues to grow at 8-10% per year.

Of the more than 5,000 hospitals in the United States, over 80% have 4 to 6 operating rooms. The remaining hospitals have between 6 and 70 operating rooms. It may be that at least half of the estimated 30,000 operating rooms in the United States are equipped to perform endoscopic surgery. In addition to hospital operating rooms, there exist more than 14,000 medical offices with surgery suites. Again, it may be that half of these office-based surgery facilities perform endoscopic procedures. Collectively, these hospitals and surgery centers may provide more than 20,000 endoscopic operating rooms to form the 12,000 unit principal market for the invention.

A secondary market involves third-party endoscope repair organizations. Often these repair companies enter into contracts with hospitals and surgical centers to capitate repair expenses for endoscopes. Such contracts may guarantee that all the endoscopes in a facility are kept in working order. The installation of an endoscopic illumination test device at these contract facilities may enable both the hospital and the repair company to quantitatively assess the endoscopic devices before and after repair, reducing unneeded repair costs.

Endoscopes are complex optical instruments, many containing more than 30 tiny lens components. By their very nature, these devices are prone to failure from:
Overstressing during surgery (particularly orthopedic)
Carelessness during sterilization reprocessing
Poor manufacturing design or workmanship
Wear-and-tear after many sterilization cycles.
Improper repair, especially by unauthorized repair facilities With costs for endoscopes ranging from $2,000 to more than $20,000, it is important to efficiently repair and keep endoscopes in use as long as possible.

There are three products that seek to address the need for quantitative endoscope measurements. None, however, meet the market need for a cost-effective device that can be used in a clinical environment. One such product is the Lighthouse Imaging Corporation EndoBench™ tester. The advantage of the EndoBench™ tester is that it provides substantial clinically significant data to determine if an endoscope is suitable for surgery. Its cost and complexity, however, make it most suitable to a manufacturing environment.

Premise Development Corporation advertises a device called the Endotester™. Like the EndoBench™ tester, this instrument performs many important optical measurements. Unfortunately, the Endotester™ requires a custom computer system and is at least as complicated as the EndoBench™. In addition, the Endotester™ is still in breadboard form and does not perform calibrated measurements, making the device of limited value in comparing test endoscopes to reference endoscopes.

BC Group manufactures the EndoCheck.™. The EndoCheck.™., however, uses a lens to project an image of the surface of the light guide or endoscope fibers which can be used to estimate the fraction of broken fibers or it can be attached to a detector to estimate the light throughput. This system, however, cannot be calibrated to determine quantitatively the output of the light guide or endoscope. Further, the EndoCheck.™. cannot be used to measure the output of the light source, which is essential in measuring the quality of the light guides and endoscopes.

Thus, a heretofore unaddressed need exists in the industry to address the aforementioned deficiencies and inadequacies.

SUMMARY OF THE INVENTION

Embodiments of the present invention provide a system and method for testing illumination quality of optic devices utilizing a light source. Briefly described, in architecture, one embodiment of the system, among others, can be implemented as follows. The endoscopic illumination tester contains an optical bridge that is removably interlockable with the light source. The endoscopic illumination tester includes an integrating sphere that is removably interlockable with the optical bridge.

The present invention can also be viewed as providing methods for testing illumination quality of optic devices utilizing a light source. In this regard, one embodiment of such a method, among others, can be broadly summarized by the following steps: inserting an optical bridge in a light emitter; and connecting an integrating sphere to the optical bridge.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
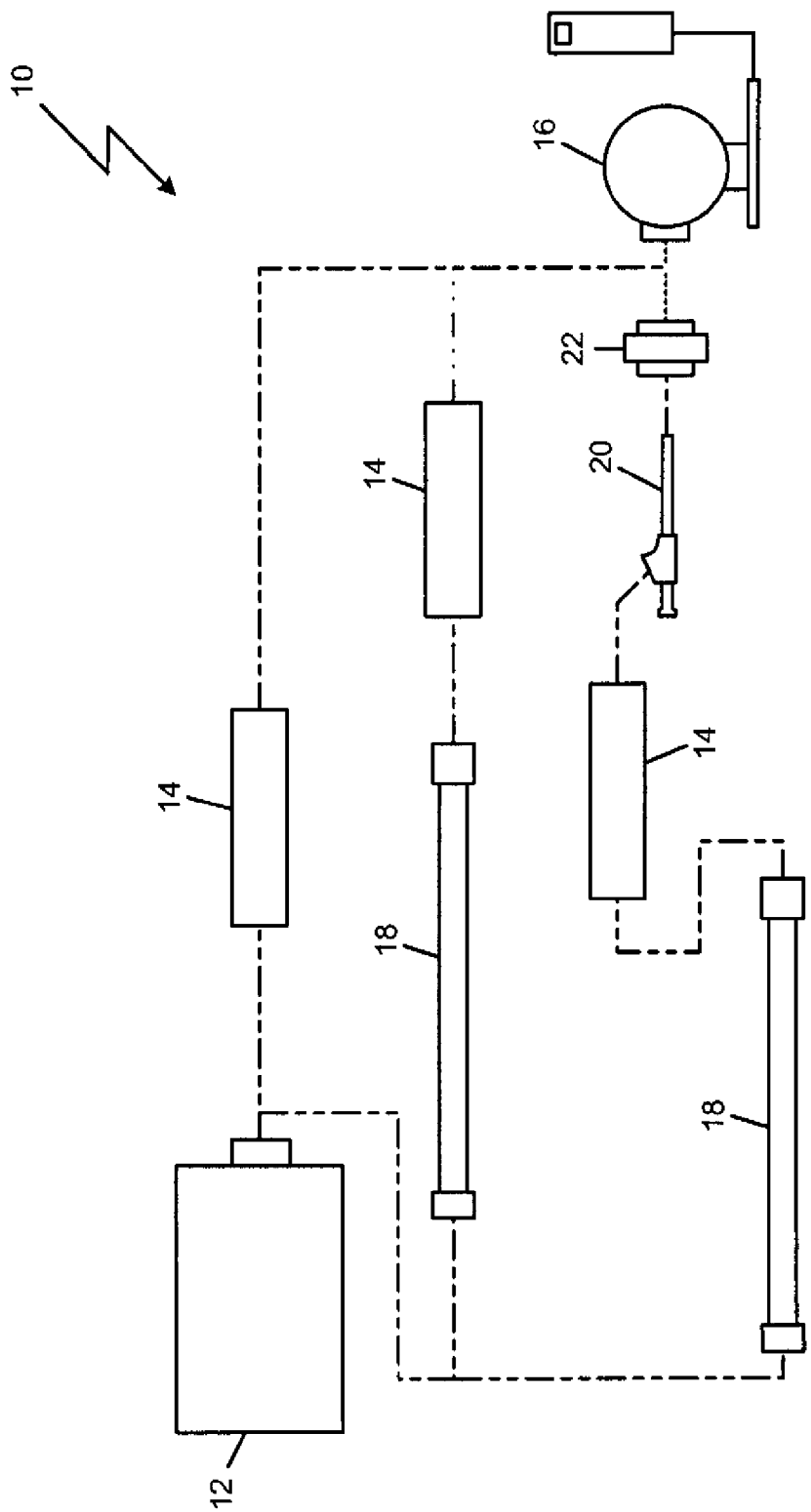
FIG. 1 is an exploded plan view of an endoscopic illumination tester, in accordance with various exemplary embodiments of the present invention.

FIG. 1 is an exploded plan view of an endoscopic illumination tester 10, in accordance with a first exemplary embodiment of the present invention. The endoscopic illumination tester 10 is useful for testing illumination quality of optic devices utilizing a light source 12. The endoscopic illumination tester 10 includes an optical bridge 14 that is removably interlockable with the light source 12. The endoscopic illumination tester 10 includes an integrating sphere 16 that is removably interlockable with the optical bridge 14.

Figure 2:
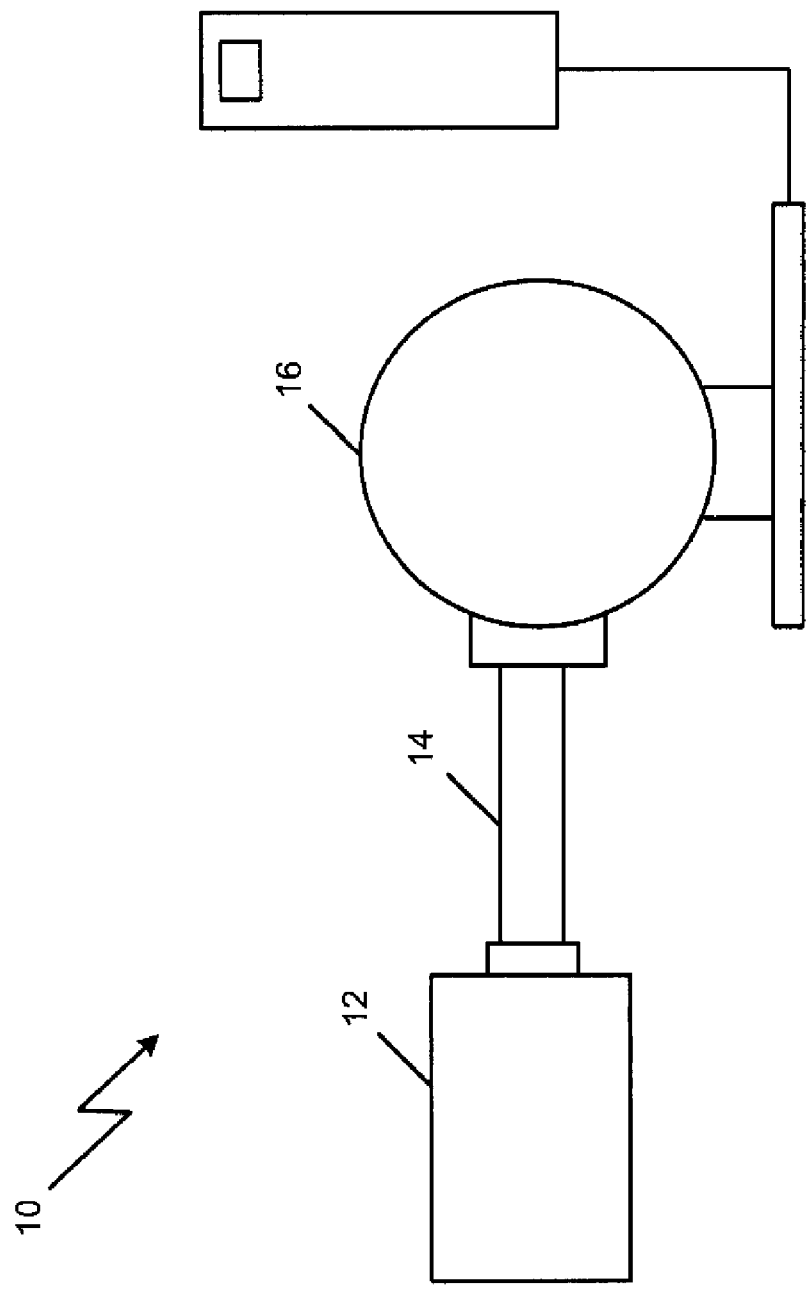
FIG. 2 is a side view of the endoscopic illumination tester of FIG. 1, in accordance with a first exemplary embodiment of the present invention.

FIG. 2 is a side view of the endoscopic illumination tester 10 of FIG. 1, in accordance with a first exemplary embodiment of the present invention. As can be seen in FIG. 1 and FIG. 2, one arrangement for testing illumination quality of optic devices utilizing a light source 12 may involve connecting the light source 12 to the optical bridge 14 and the optical bridge 14 to the integrating sphere 16. This connection will allow the integrating sphere 16 to get a reading on the lumen available directly from the light source 12. The optical bridge 14 may be inserted into the light source 12 until a first end of the optical bridge 14 is proximately at a focus of the optics of the light source 12. Proximately at a focus of the optics of the light source 12 may be interpreted to mean within 1 mm of the light source 12. Proximately at a focus of the optics of the light source 12 is generally the same objective sought for locating a light guide within the light source 12. Therefore, proximately at a focus of the optics of the light source 12 may also be understood to mimicking the positioning of a light guide within the light source 12.

The light source 12 may mechanically interlock with the optical bridge 14 in a manner that makes it easy to locate the first end of the optical bridge 14 proximate to the focus of the optics of the light source 12. Similarly, a second end of the optical bridge 14 may be inserted in the integrating sphere 16 such that a face of the second end is approximately even with an inner wall of the integrating sphere 16. Approximately even with an inner wall of the integrating sphere 16 may be interpreted to mean within 1 mm of this location.

Figure 3:
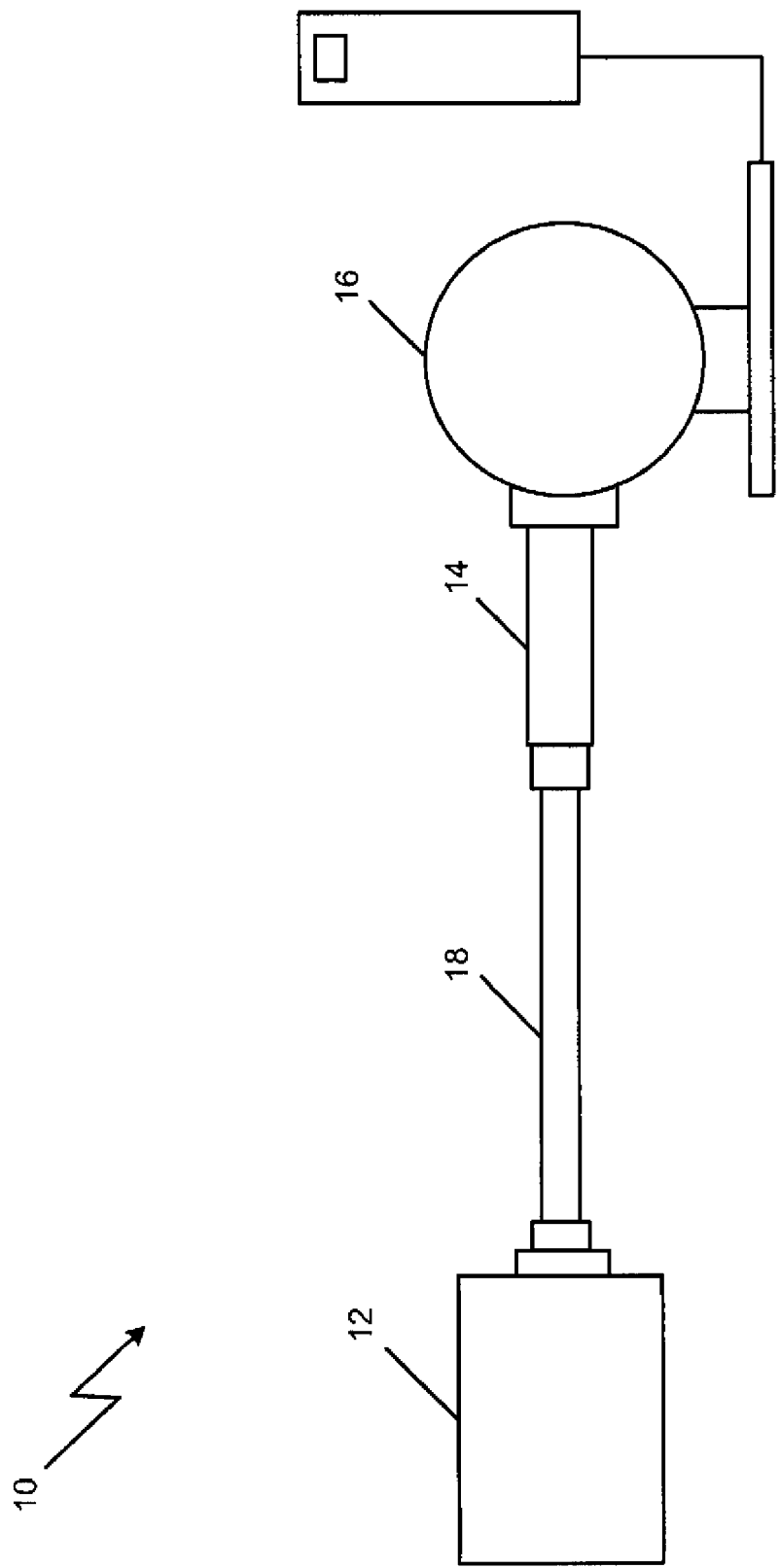
FIG. 3 is a side view of the endoscopic illumination tester of FIG. 1, in accordance with a second exemplary embodiment of the present invention.

FIG. 3 is a side view of the endoscopic illumination tester 10 of FIG. 1, in accordance with a second exemplary embodiment of the present invention. One may wish to get an illumination quality reading for the illumination available from a light guide 18, which may be typically attached to the light source 12. As can be seen from FIG. 1 and FIG. 3, to test the illumination quality from the light guide 18, the light guide 18 may, at opposing ends, be connected to the light source 12 and the optical bridge 14 and the optical bridge 14 may be connected to the integrating sphere 16. Getting an illumination reading from the light source 12 independently and from the light source 12 in combination with a light guide 18 may help determine whether the light guide 18 has a light transmissivity problem.

Figure 4:
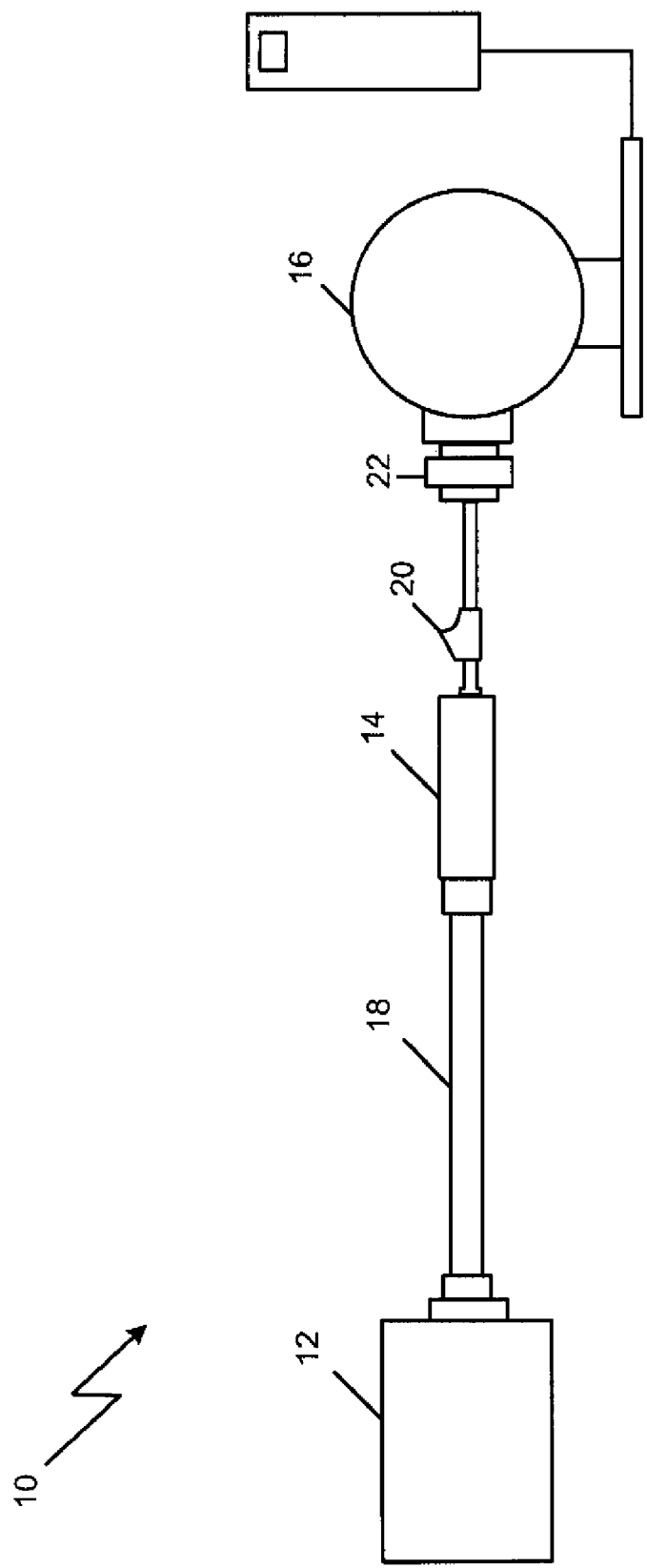
FIG. 4 is a side view of the endoscopic illumination tester of FIG. 1, in accordance with a third exemplary embodiment of the present invention.

FIG. 4 is a side view of the endoscopic illumination tester 10 of FIG. 1, in accordance with a third exemplary embodiment of the present invention. As can be seen in FIG. 1 and FIG. 4, a further arrangement for the endoscopic illumination tester 10 is available. Specifically, an endoscope 20 may be included in the testing to evaluate light transmissivity of the endoscope 20. In this third arrangement, the light source 12 is connected to the light guide 18, the light guide 18 is connected to the optical bridge 14, the optical bridge 14 is connected to the endoscope 20, and the endoscope 20 is connected to the integrating sphere 16.

Endoscopes 20 are made in varying shapes and sizes, with diameters ranging generally from 2 mm to 15 mm. To allow most endoscopes 20 to be functional with the present invention, a scope clamp 22 is provided. The scope clamp 22 secures to both the integrating sphere 16 and the endoscope 20 to hold the endoscope 20 securely to and within the integrating sphere 16. The endoscope 20 may be secured in a position such that a tip of the endoscope 20 is within the integrating sphere 16. Further, when secured with the scope clamp 22, the tip of the endoscope 20 should be positioned such that it is not abutting a wall within the integrating sphere 16 in a manner that would interfere with radiant emissions from the tip of the endoscope 20.

In the manner described, the endoscopic illumination tester 10 quantitatively measures the fitness of an endoscope 20 for use in surgical procedures by measuring the illumination level in various parts of the system, namely the output of the light source 12, output of the light guide 18, and output of the endoscope 20. It should be noted that for simplicity, we refer to the devices under test as endoscopic devices or endoscopes 20. However, the invention applies equally well to borescopic devices and borescopes that, for the purposes of this description, are operative equivalents to endoscopic systems. The endoscopic illumination tester 10 may be effectively used to test the optical quality of various optic devices, as would be recognized by one of ordinary skill in the art.

Endoscopic light sources 12 are generally configured such that light guide 18 can be repeatedly attached to the light source 12 output port through the use of standard adapters. The most common adapters include those manufactured by ACMI, Wolf, Storz, and Olympus, the primary providers of endoscope equipment. Many endoscopic light sources 12 contain turrets, which may allow any one of the common adapters to be used by simply rotating the turret into the proper position. Unfortunately, the use of these standard output port adapters makes it difficult to accurately measure the light output luminance since the optimal location of the measurement is located inside the light source 12 and is inaccessible to commonly available photometers.

The endoscopic illumination tester 10 uses an optical bridge 14 to transfer the illumination from the optimal location inside the light source 12 to a position outside the light source 12 where it can be conveniently and repeatedly connected to the photometer part of the endoscopic illumination tester 10 through the use of custom adapters.

A similar problem as above occurs when trying to measure the light output of a light guide 18. Endoscopic light guides 18 are generally configured such that light guides 18 can be repeatedly attached to the endoscope 20 fiber optic input port through the use of standard adapters. The most common adapters include those manufactured by ACMI, Wolf, and Storz. Again, unfortunately, the use of these standard endoscope 20 input adapters makes it difficult to accurately measure the light output luminance since the optimal location of the measurement is located inside the light guide 18 adapter and is inaccessible to commonly available photometers. The endoscopic illumination tester 10 uses the same optical bridge 14 as above to transfer the illumination from the optimal location inside the light guide 18 adapter to a position outside the light guide 18 where it can be conveniently and repeatedly connected to the photometer part of the endoscopic illumination tester 10 through the use of other custom adapters.

Another measurement that is useful for the endoscopic illumination tester 10 is the measurement of the output from a distal tip of the endoscope 20 itself. In this case, the wide variety of diameters of commercially available endoscopes 20 precludes the use of standard adapters as were used for the light source 12 and light guide 18 measurements above. In this measurement, the optical bridge 14 is also used, however, as it allows quantitative comparison with the measurements conducted on the output of the light guide 18. In other words, because the optical bridge 14 attenuates the light emitted from the light guide 18, including the optical bridge 14 in the process when making the endoscope 20 measurement helps to avoid a systematic error.

Further, as the present invention is designed to test optical properties of the light source 12, the light guide 18, the endoscope 20, and other preexisting equipment, the present invention may be described as a kit providing the optical bridge 14, the integrating sphere 20, and, optionally, the scope clamp 22 to be assembled with preexisting equipment as described herein.

Figure 5:
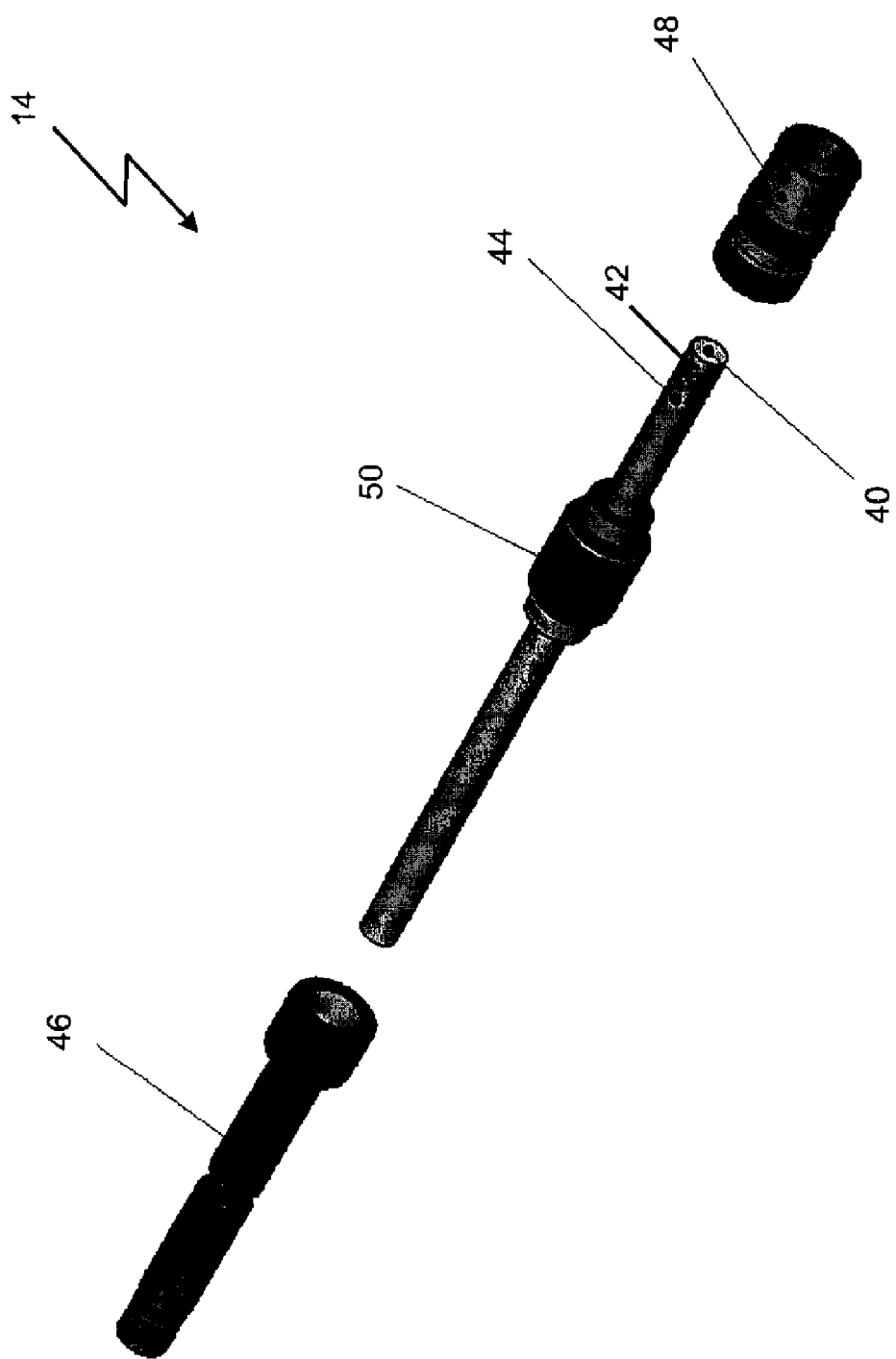
FIG. 5 is an exploded perspective view of the optical bridge of FIG. 1, in accordance with the first exemplary embodiment of the present invention.

FIG. 5 is an exploded perspective view of the optical bridge 14 of FIG. 1, in accordance with the first exemplary embodiment of the present invention. The optical bridge 14 includes a cylindrical core rod 40 of glass with a surrounding cladding 42 of a different glass of lower refractive index than the core 40. The ends of the optical bridge 14 are ground and polished. This allows the optical bridge 14 to operate like an optical fiber, only bigger. Light that is input into one end of the optical bridge 14 is transmitted by total internal reflection to the other end of the optical bridge 14. The cladding 42 of the optical bridge 14 may be surrounded by a metal or plastic sheathe 44. The sheathe 44 may have external threads to allow various standard connectors 46, 48 to be attached. A handle portion 50 of the optical bridge 14 may allow handling of the optical bridge 14 and connection to an input adapter 46 and/or an output adapter 48 by helical threading in the adapters or other mechanical connection means, as is known to those having ordinary skill in the art. The optical portion 40, 42 of the optical bridge 14 may be made of a bundle of small optical fibers that are epoxied into the sheathe 44, however repeatability of measurements may be improved by using a solid optical bridge 14 rather than a bundle of smaller optical fibers.

Figure 6:
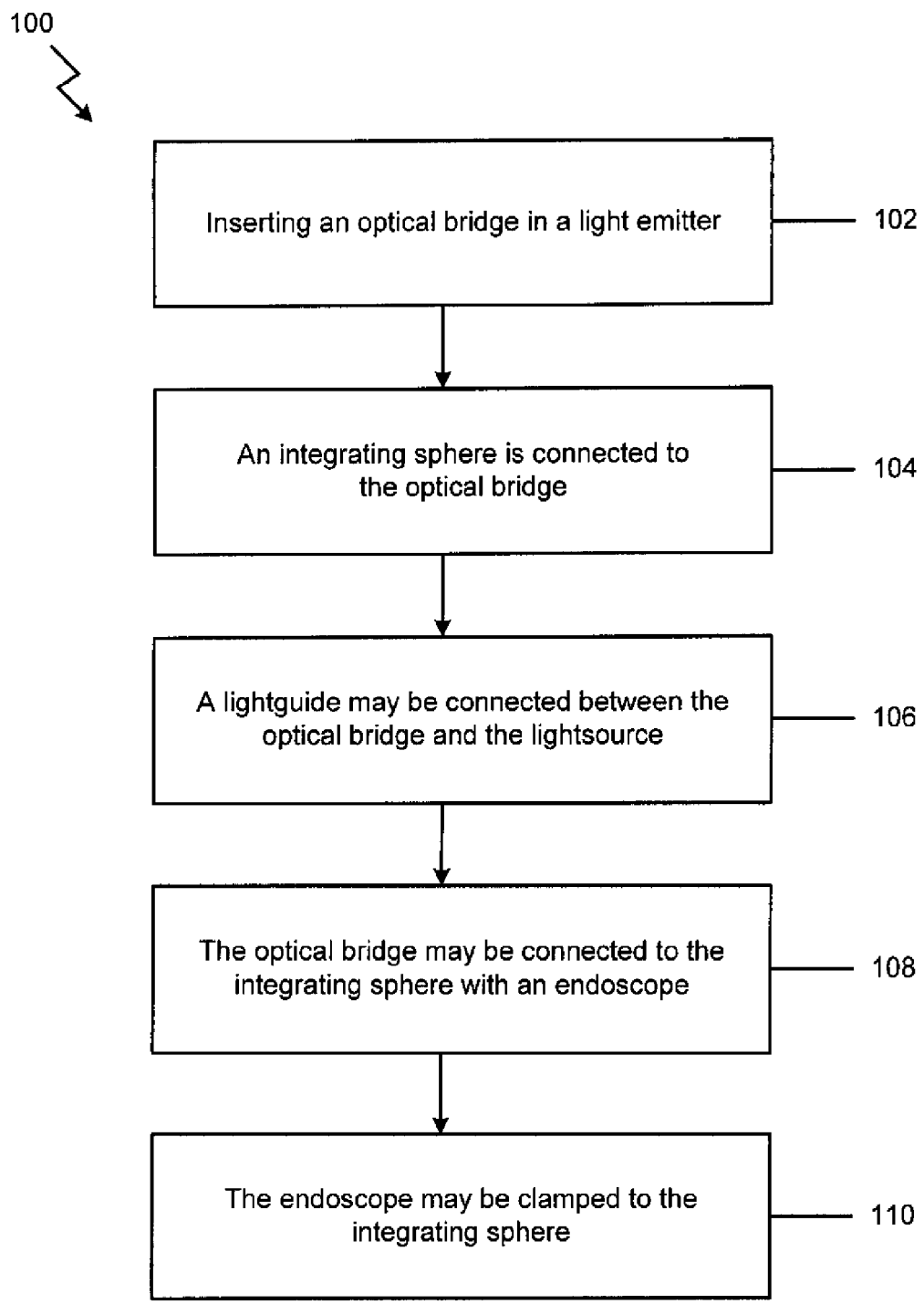
FIG. 6 is a flowchart illustrating a method of testing illumination quality of a light source, in accordance with the first exemplary embodiment of the invention.

FIG. 6 is a flowchart 100 illustrating a method of providing the abovementioned endoscopic illumination tester 10 in accordance with the first exemplary embodiment of the invention. It should be noted that any process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently or in reverse order, depending on the functionality involved, as would be understood by those reasonably skilled in the art of the present invention.

As is shown by block 102, a method of testing illumination quality of a light source 12 includes inserting an optical bridge 14 in a light emitter 12. An integrating sphere 16 is connected to the optical bridge 14 (block 104). Further, a light guide 18 may be connected between the optical bridge 14 and the light source 12 (block 106). Further, the optical bridge 14 may be connected to the integrating sphere 16 with an endoscope 20 (block 108). Further, the endoscope 20 may be clamped to the integrating sphere 16 (block 110).

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A system for testing illumination quality of an optic device having a light source, the system comprising:
  a cylindrical core glass rod having a first end and second end, wherein the cylindrical core glass rod is removably interlockable to the light source of the optic device, wherein the first end of the cylindrical core glass rod is proximately at a focus of an optic of the light source, wherein the cylindrical core glass rod is exclusive of the optic device, and wherein light that is input into the first end is transmitted to the second end; and
  an integrating sphere removably interlockable to the second end of the cylindrical core glass rod.

2. The system of claim 1, wherein the cylindrical core glass rod at least partially penetrates the light source.

3. The system of claim 1, wherein the cylindrical core glass rod at least partially penetrates the integrating sphere.

4. The system of claim 1, wherein the cylindrical core glass rod is positioned to gain access to a focal point inside the light source.

5. The system of claim 1, wherein the cylindrical core glass rod is surrounded by a cladding.

6. The system of claim 1, wherein the cylindrical core glass rod is surrounded by a glass cladding.

7. The system of claim 1, wherein the optic device includes a light guide removably interlocking the cylindrical core glass rod to the light source.

8. The system of claim 1, wherein the optic device includes an endoscope connecting the cylindrical core glass rod to the integrating sphere.

9. The system of claim 6, wherein the glass cladding has a lower refractive index than the cylindrical core glass rod.

10. The system of claim 7, wherein the cylindrical core glass rod at least partially penetrates one opening of the light guide.

11. The system of claim 7, wherein the cylindrical core glass rod attenuates a light emitted through the light guide.

12. The system of claim 8, wherein the endoscope at least partially penetrates the integrating sphere.

13. The system of claim 8, wherein the optic device includes a scope clamp securing the endoscope to the integrating sphere.

14. A kit for testing optical quality of an optic device having a light source, the kit comprising:
  a cylindrical core glass rod having a first end and second end, wherein the core glass rod is removably interlockable with the light source of the optic device, wherein the first end of the cylindrical core glass rod is proximately at a focus of an optic of the light source, wherein the cylindrical core glass rod is exclusive of the optic device, and wherein light that is input into the first end is transmitted to the second end; and
  an integrating sphere removably interlockable to the second end of the cylindrical core glass rod.

15. The kit of claim 14, wherein the optic device includes a scope clamp removably securable to the integrating sphere and concurrently removably securable to an endoscope of the optic device, thereby permitting optical testing of the endoscope.

16. The kit of claim 14, wherein the cylindrical core glass rod is further mateable with a light guide of the optic device, thereby permitting optical testing of the light guide.

17. A method of testing illumination quality of an optic device having a light source, the method comprising the steps of:

removably interlocking a cylindrical core glass rod to the light source, wherein the cylindrical core glass rod has a first end and a second end, wherein the first end of the cylindrical core glass rod is proximately at a focus of an optic of the light source, wherein the cylindrical core glass rod is exclusive of the optic device, and light that is input into the first end is transmitted to the second end; and removably interlocking an integrating sphere to the second end of the cylindrical core glass rod.

18. The method of claim 17, further comprising removably interlocking the cylindrical core glass rod to the light source by connecting a light guide of the optic device between the cylindrical core glass rod and the light source, thereby permitting optical testing of the light guide.

19. The method of claim 17, further comprising removably interlocking the cylindrical core glass rod to the integrating sphere by connecting the cylindrical core glass rod to the integrating sphere with an endoscope of the optic device, thereby permitting optical testing of the endoscope.

20. The method of claim 19, further comprising clamping the endoscope to the integrating sphere.

* * * * *